United States Patent
Govari et al.

(10) Patent No.: US 11,653,973 B2
(45) Date of Patent: *May 23, 2023

(54) CATHETER DISTAL END MADE OF PLASTIC TUBE AND FLEXIBLE PRINTED CIRCUIT BOARDS

(71) Applicant: Biosense Webster (Israel) Ltd., Yokneam (IL)

(72) Inventors: Assaf Govari, Haifa (IL); Andres Claudio Altmann, Haifa (IL); Yehuda Algawi, Binyamina (IL); Ilya Sitnitsky, Nahariya (IL); Christopher Thomas Beeckler, Brea, CA (US); Joseph Thomas Keyes, Sierra Madre, CA (US); Kevin Justin Herrera, West Covina, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 135 days.

This patent is subject to a terminal disclaimer.

(21) Appl. No.: 17/156,417

(22) Filed: Jan. 22, 2021

(65) Prior Publication Data

US 2021/0137594 A1    May 13, 2021

Related U.S. Application Data

(63) Continuation of application No. 15/333,853, filed on Oct. 25, 2016, now Pat. No. 10,898,262.

(51) Int. Cl.
*A61B 18/14* (2006.01)
*A61B 5/283* (2021.01)
(Continued)

(52) U.S. Cl.
CPC .......... *A61B 18/1492* (2013.01); *A61B 5/036* (2013.01); *A61B 5/065* (2013.01);
(Continued)

(58) Field of Classification Search
CPC . A61B 5/0408; A61B 5/04085; A61B 5/0478; A61B 5/0492; A61B 5/0422;
(Continued)

(56) References Cited

U.S. PATENT DOCUMENTS 5,507,725 A * 4/1996 Savage ............. A61M 25/0147
604/95.04
6,695,808 B2  2/2004 Tom
(Continued)

FOREIGN PATENT DOCUMENTS

CN    101243968 A    8/2008
CN    101332083 A    12/2008
(Continued)

OTHER PUBLICATIONS

Extended European Search Report dated Mar. 13, 2018, from corresponding European application No. 17197945.3.
(Continued)

*Primary Examiner* — Daniel W Fowler
*Assistant Examiner* — Bradford C. Blaise
(74) *Attorney, Agent, or Firm* — Troutman Pepper hamilton Sanders LLP

(57) ABSTRACT

A catheter includes an insertion tube, a flexible substrate and one or more electrical devices. The insertion tube is configured for insertion into a patient body. The flexible substrate is configured to wrap around a distal end of the insertion tube and includes electrical interconnections. The electrical devices are coupled to the flexible substrate and are connected to the electrical interconnections.

11 Claims, 3 Drawing Sheets

(51) Int. Cl.
  *A61B 5/03* (2006.01)
  *A61B 5/06* (2006.01)
  *A61B 5/00* (2006.01)
  *A61M 25/00* (2006.01)
  *A61B 18/00* (2006.01)
  *A61M 25/02* (2006.01)

(52) U.S. Cl.
  CPC ............ *A61B 5/283* (2021.01); *A61B 5/6852* (2013.01); *A61M 25/0067* (2013.01); *A61B 2018/00351* (2013.01); *A61B 2018/00577* (2013.01); *A61B 2018/00815* (2013.01); *A61B 2018/00821* (2013.01); *A61B 2018/00839* (2013.01); *A61B 2018/00875* (2013.01); *A61B 2018/1465* (2013.01); *A61B 2018/1467* (2013.01); *A61B 2218/002* (2013.01); *A61B 2560/00* (2013.01); *A61B 2560/04* (2013.01); *A61B 2560/0462* (2013.01); *A61B 2560/0468* (2013.01); *A61B 2562/0209* (2013.01); *A61B 2562/164* (2013.01); *A61B 2562/166* (2013.01); *A61M 25/0043* (2013.01); *A61M 25/0068* (2013.01); *A61M 2025/0063* (2013.01); *A61M 2025/028* (2013.01); *A61M 2210/125* (2013.01)

(58) Field of Classification Search
  CPC ....... A61B 5/6852; A61B 5/0215; A61B 5/04; A61B 8/12; A61B 18/1492; A61B 2018/0212; A61B 2018/1467; A61B 2018/1465; A61B 2560/00; A61B 2560/04; A61B 2560/0462; A61B 2560/0468; A61B 2562/00; A61B 2562/0209; A61B 2562/04; A61B 2562/043; A61B 2562/046; A61B 2562/06; A61B 2562/063; A61B 2562/066; A61B 2562/164; A61B 2562/166; A61B 2562/0043; A61B 2562/021; A61M 25/0009; A61M 25/0067; A61M 25/0023; A61M 25/0026; A61M 25/0043; A61M 25/0068; A61M 25/0071; A61M 2025/0057; A61M 2025/0063; A61M 2025/028
  See application file for complete search history.

(56) References Cited

U.S. PATENT DOCUMENTS

| | | | |
|---|---|---|---|
| 7,301,332 B2 | 11/2007 | Govari et al. | |
| 7,881,769 B2 | 2/2011 | Sobe | |
| 8,147,486 B2 * | 4/2012 | Honour | A61N 1/05 606/41 |
| 3,221,408 A1 | 7/2012 | Johnson et al. | |
| 3,560,086 A1 | 10/2013 | Just et al. | |
| 9,037,264 B2 | 5/2015 | Just et al. | |
| 9,179,971 B2 | 11/2015 | Kirschenman | |
| 9,226,688 B2 | 1/2016 | Jacobsen et al. | |
| 9,687,297 B2 | 6/2017 | Just et al. | |
| 10,898,262 B2 * | 1/2021 | Govari | A61B 5/065 |
| 2007/0167824 A1 | 7/2007 | Lee et al. | |
| 2007/0219551 A1 | 9/2007 | Honour et al. | |
| 2009/0143651 A1 | 6/2009 | Kallback et al. | |
| 2010/0049191 A1 | 2/2010 | Habib et al. | |
| 2010/0305420 A1 | 12/2010 | Curry | |
| 2012/0157991 A1 | 6/2012 | Christian | |
| 2014/0163546 A1 * | 6/2014 | Govari | A61B 18/1206 606/41 |
| 2015/0073409 A1 | 3/2015 | Watson et al. | |
| 2015/0157400 A1 | 6/2015 | Gelbart et al. | |
| 2015/0351832 A1 | 12/2015 | Oliverius et al. | |
| 2016/0113712 A1 | 4/2016 | Cheung et al. | |
| 2016/0228061 A1 * | 8/2016 | Kallback | A61B 5/0215 |
| 2016/0270732 A1 | 9/2016 | Kallback et al. | |
| 2016/0317094 A1 * | 11/2016 | Byrd | A61B 5/0538 |
| 2017/0319270 A1 | 11/2017 | Just et al. | |

FOREIGN PATENT DOCUMENTS

| | | |
|---|---|---|
| EP | 1502542 A1 | 2/2005 |
| EP | 1671669 B1 | 5/2008 |
| EP | 1714610 B1 | 12/2011 |
| EP | 2742891 A1 | 6/2014 |
| JP | 2000083918 A | 3/2000 |
| JP | 2012505041 A1 | 10/2008 |
| JP | 2014506169 A | 3/2014 |
| JP | 2017501843 A | 1/2017 |
| WO | 2015106116 A1 | 1/2014 |
| WO | 2016095810 A1 | 6/2016 |

OTHER PUBLICATIONS

Search Report dated Feb. 11, 2019, from corresponding European application No. 17197945.3.
Notification of Reasons for Refusal dated Sep. 14, 2021, from corresponding Japnese application No. 2017-205026.
First Office action dated Jan. 14, 2022, from corresponding Chinese application No. 201711008402.6.

* cited by examiner

CATHETER DISTAL END MADE OF PLASTIC TUBE AND FLEXIBLE PRINTED CIRCUIT BOARDS

CROSS-REFERENCE TO RELATED APPLICATION(S)

This application is a CONTINUATION application under 35 USC 120 of U.S. patent application Ser. No. 15/333,853, filed Oct. 25, 2016, granted as U.S. Pat. No. 10,898,262, the entire contents of which are incorporated herein by reference.

FIELD OF THE INVENTION

The present invention relates generally to catheter distal ends, and particularly to distal ends made of a flexible substrate.

BACKGROUND OF THE INVENTION

Catheters may be used in various medical applications, such as cardiology. For example, U.S. Patent Application Publication 2015/0157400, whose disclosure is incorporated herein by reference, describes a device positionable in a cavity of a bodily organ (e.g., a heart) that may discriminate between fluid (e.g., blood) and non-fluid tissue (e.g., wall of heart) to provide information or a mapping indicative of a position and/or orientation of the device in the cavity. The device may include a plurality of transducers, intravascularly guided in an unexpanded configuration and positioned proximate the non-fluid tissue in an expanded configuration. Expansion mechanism may include helical member(s) or inflatable member(s).

U.S. Pat. No. 7,881,769, whose disclosure is incorporated herein by reference, describes a catheter for performing a medical operation on an organic lumen. The catheter includes an elongated member, a medical operational element located at a distal end of the elongated member, an electromagnetic field detector located at the distal end, and a wiring for coupling the electromagnetic field detector with a medical positioning system, wherein the medical positioning system determines the position and orientation of the distal end.

U.S. Patent Application Publication 2010/0049191, whose disclosure is incorporated herein by reference, describes an electromagnetic energy delivery device which is deployable through an elongate channel extending along a flexible endoscope for delivering electromagnetic energy to tissue. The device has an elongate main body and an electrode assembly at a distal end of the device. The main body of the device is flexible along the length of the device to enable the device to conform to the shape of a channel of a flexible endoscope.

SUMMARY OF THE INVENTION

An embodiment of the present invention provides a catheter including an insertion tube, a flexible substrate and one or more electrical devices. The insertion tube is configured for insertion into a patient body. The flexible substrate is configured to wrap around a distal end of the insertion tube and includes electrical interconnections. The electrical devices are coupled to the flexible substrate and are connected to the electrical interconnections.

In some embodiments, the insertion tube is made of plastic. In some embodiments, the insertion tube is hollow so as to form an internal lumen for leading one or more electrical wires to the distal end. In an embodiment, the insertion tube is hollow so as to form an internal lumen for leading one or more irrigation tubes to the distal end.

In a disclosed embodiment, the flexible substrate includes a flexible printed circuit board (PCB), and the electrical interconnections include conductive traces. In an embodiment, the flexible substrate includes one or more films that plate the distal end so as to form at least some of the electrical interconnections and the electrical devices. In another embodiment, the flexible substrate is perforated so as to form irrigation holes.

In an embodiment, the electrical devices include one or more electrodes. Additionally or alternatively, the electrical devices may include one or more thermocouples. Further additionally or alternatively, the electrical devices may include one or more thermistors. Further additionally or alternatively, the electrical devices may include one or more pressure sensors. Further additionally or alternatively, the electrical devices may include one or more position sensors.

In some embodiments, the flexible substrate includes a sheet having first and second edges, and a dome-cover, the sheet is configured to wrap around the distal end of the insertion tube, and the dome-cover is configured to cover an apex of the distal end. In an embodiment, the sheet and the dome-cover are made of a single contiguous section of the flexible substrate. In another embodiment, the first and second edges of the sheet are welded to one another when wrapped around the distal end. In yet another embodiment, the dome-cover is glued to the apex of the distal end. In still another embodiment, the dome-cover is made of a liquid crystal polymer (LCP) PCB, which is configured to be formed into a cup shape, and the cup shape is configured to be bonded to the apex of the distal end.

There is additionally provided, in accordance with an embodiment of the present invention, a method for producing a catheter. The method includes providing an insertion tube, and wrapping a flexible substrate around a distal end of the insertion tube. The flexible substrate includes one or more electrical interconnections. One or more electrical devices are coupled to the flexible substrate, and the electrical devices are connected to the electrical interconnections.

The present invention will be more fully understood from the following detailed description of the embodiments thereof, taken together with the drawings in which:

DETAILED DESCRIPTION OF EMBODIMENTS

Overview

Figure 1:
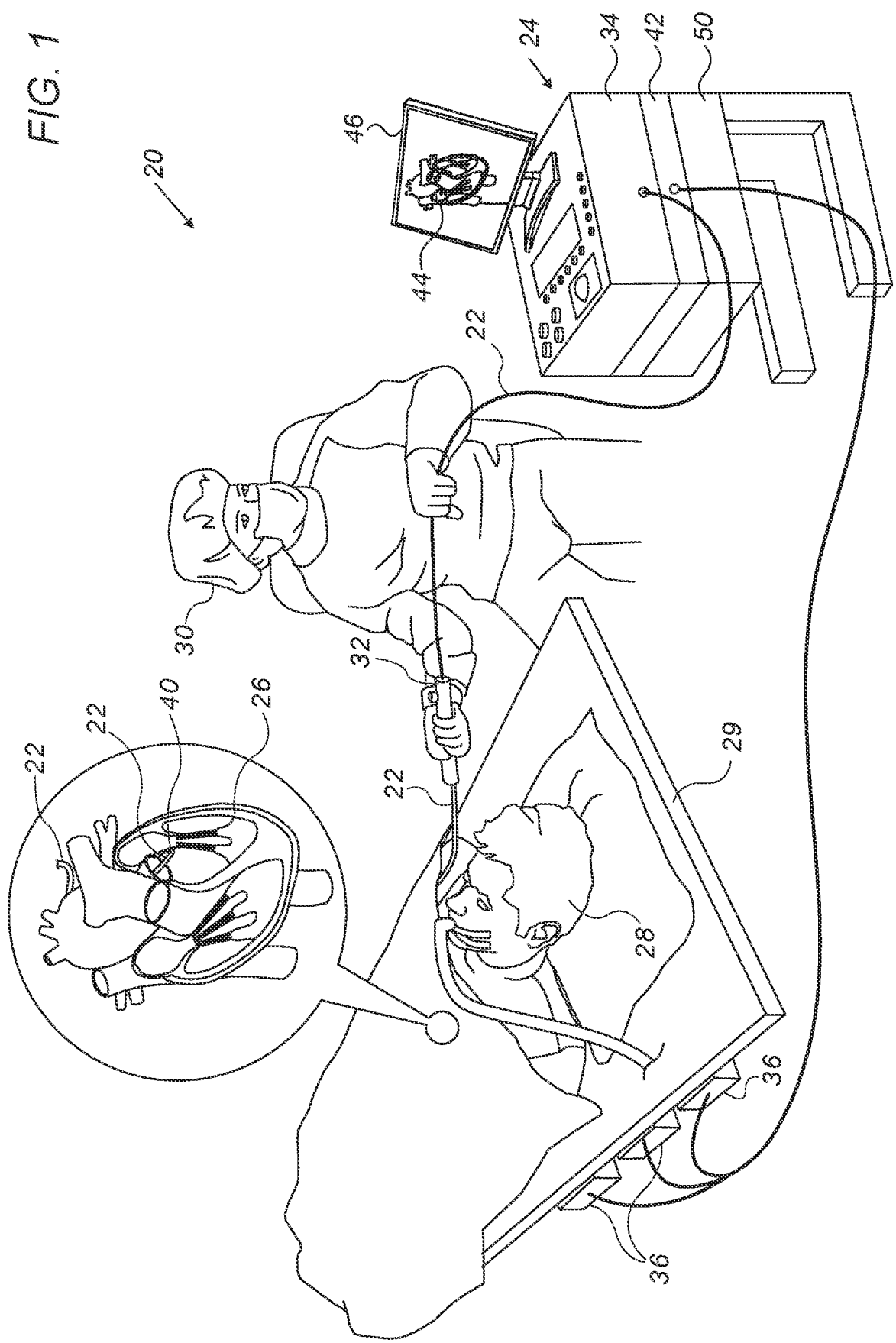
FIG. 1 is a schematic, pictorial illustration of a catheterization system, in accordance with an embodiment of the present invention.

Medical probes such as catheters are used in a variety of therapeutic and diagnostic medical procedures, for example in cardiac ablation. Catheter distal ends are often multi-functional and comprise a large number of elements such as different types of electrodes, electrical interconnections for the electrodes, irrigation tubes and holes. The distal end is typically limited in size, this limits the functionality that can be incorporated therein.

Embodiments of the present invention that are described hereinbelow provide improved distal end assembly configurations for medical probes, which overcome the above limitations. In some embodiments, the distal end assembly is fabricated from a single sheet of a flexible substrate that provides various functionalities within a small volume such as: (i) forms a mechanical substrate for mounting or embedding electrical devices such as electrodes or sensors, (ii) comprises conducting traces that convey electrical signals to/from the electrical devices, and/or (iii) comprises irrigation tubes and holes for irrigating the tissue area. The disclosed techniques further describe methods for producing these catheter distal ends.

The distal end assembly typically comprises a cylindrical insertion tube having a cover on its top. In some embodiments, the insertion tube comprises an inner skeleton structure and the cylindrical shape of the tube is formed by wrapping a sheet of flexible substrate, such as a multi-layered printed circuit board (PCB), around the skeleton structure.

In some embodiments, at least some of the electrical wiring of the distal end is implemented using circuit traces in or on the flexible PCB. The traces are configured to electrically connect the electrical devices coupled to the PCB (e.g., electrodes or sensors) to wiring that traverse the catheter. Some types of electrical devices (e.g., thermocouples) may be embedded between the PCB layers. Other devices, such as micro-electrodes, may be mounted on the PCB surface before or after wrapping the PCB around the insertion tube. In other embodiments, the PCB may be perforated so as to form irrigation holes.

In an embodiment, the PCB comprises a sheet having two edges, and a dome-cover. The sheet is configured to wrap around the skeleton structure of the insertion tube and the two edges are attached to one another by welding or using any other suitable coupling technique. In some embodiments, the dome-cover may be glued to the apex of the distal end assembly and may comprise irrigation holes and one or more tip-electrodes mounted thereon. In alternative embodiments, the dome-cover may be fabricated from a liquid crystal polymer (LCP) PCB, which may be thermoformed into a cup shape and bonded to the apex. The sheet and the dome-cover may be formed as a single contiguous piece of the PCB, or as separate parts that may be coupled to one another after being wrapped around the distal end assembly.

In an alternative embodiment, the distal section of the insertion tube is contiguous, and the conductive traces and electrical devices described above are formed by directly plating one or more films around the insertion tube. At least the outermost film is typically biocompatible so as to allow direct physical contact between the distal end assembly and the heart. In some embodiments, the insertion tube as well as the flexible substrate may be perforated, so as to allow irrigation flow to exit the insertion tube via the irrigation holes.

The disclosed techniques help to increase the functionality of medical catheters without compromising size, as well as achieve smaller catheters for new applications. Furthermore, using very large integrated circuit (VLSI) techniques provides producers of the flexible substrates with high flexibility to improve the catheters and to reduce the cost of the distal end. For example, the disclosed techniques enable integration of all electrical devices and interconnections in a flexible substrate wrapped around a low cost molded plastic assembly rather than producing expensive micro-machined metal tubes, wires and electrodes, and mounting them on the metal tube.

SYSTEM DESCRIPTION

FIG. 1 is a schematic, pictorial illustration of a catheterization system 20, in accordance with an embodiment of the present invention. System 20 comprises a probe 22, in the present example a cardiac catheter, and a control console 24. In the embodiment described herein, catheter 22 may be used for any suitable therapeutic and/or diagnostic purposes, such as ablation of tissue in a heart 26.

Console 24 comprises a processor 42, typically a general-purpose computer, with suitable front end and interface circuits for receiving signals from catheter 22 and for controlling the other components of system 20 described herein.

An operator 30 (such as an interventional cardiologist) inserts catheter 22 through the vascular system of a patient 28 lying on a table 29. Catheter 22 comprises a distal end assembly 40, which is depicted in details in FIGS. 2-4. Operator 30 moves assembly 40 in the vicinity of the target region in heart 26 by manipulating catheter 22 with a manipulator 32 near the proximal end of the catheter as shown in the inset of FIG. 1. The proximal end of catheter 22 is connected to interface circuitry in processor 42.

In some embodiments, the position of the distal end assembly in the heart cavity is typically measured by magnetic position sensing in catheter tracking system 20. In this case, console 24 comprises a driver circuit 34, which drives magnetic field generators 36 placed at known positions external to patient 28 lying on table 29, e.g., below the patient's torso.

Figure 2:
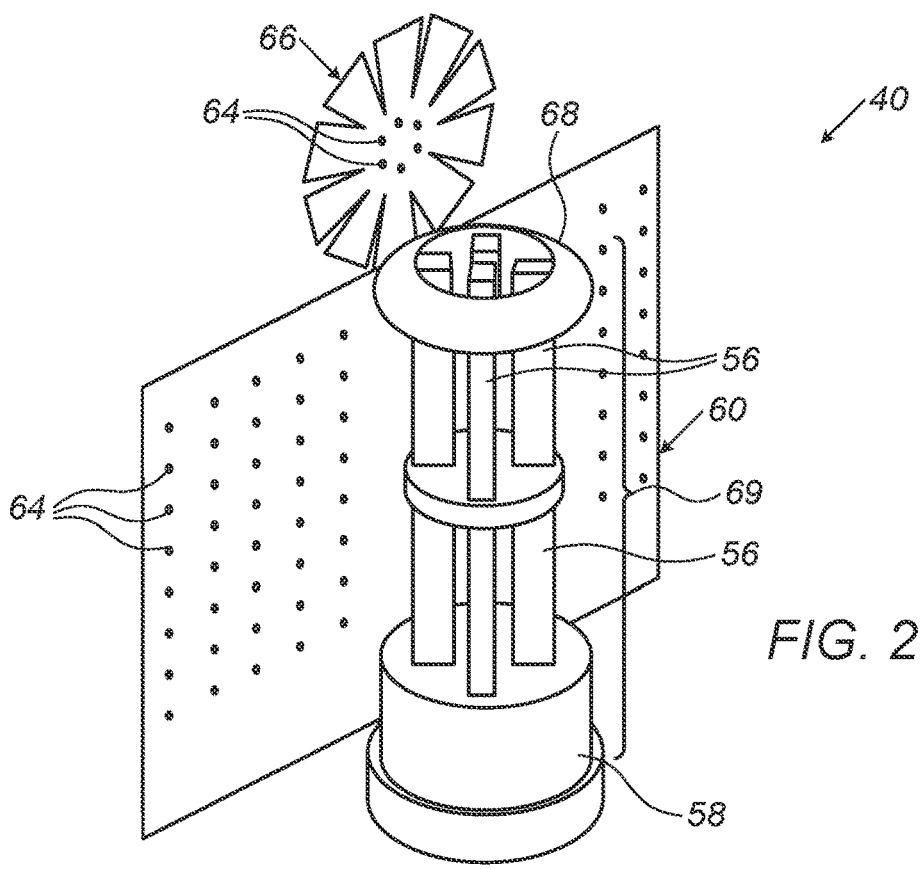
FIGS. 2 and 3 are schematic, exploded pictorial illustrations of a distal end assembly of a catheter, in accordance with an embodiment of the present invention.

FIG. 2 is a schematic, exploded pictorial illustration of distal end assembly 40, in accordance with an embodiment of the present invention. In some embodiments, distal end assembly 40 comprises an internal member 69, which may be made of plastic or any other suitable material. The internal member is also referred to herein as an insertion tube. The internal member may have a skeleton support structure as depicted in FIG. 2, or any other suitable structure as will be described in other embodiments below.

A base 58 is located at the proximal end of member 69, a ring-shaped dome-support 68 is located at the apex of member 69, and multiple ribs 56 connect the base and the dome-support. In this embodiment, member 69 has an internal lumen for directing irrigation into the inside of cavity formed by flexible printed circuit board (PCB) sheet 60.

Distal end assembly 40 further comprises a flexible substrate, such as a multi-layered flexible printed circuit board (PCB) sheet 60, which is configured to wrap around member 69. In an embodiment, after wrapping, the left and right edges of sheet 60 may be coupled to one another by welding or using any other suitable coupling technique. In some embodiments, one or more electrical devices may be mounted on PCB sheet 60, as will be depicted in FIG. 3 below.

PCB sheet 60 typically comprises electrical interconnections, such as conductive traces (not shown), which are configured to electrically connect the electrical devices coupled to the PCB to suitable wires that traverse the catheter, or to other suitable circuitry. In some embodiments, PCB sheet 60 may be perforated so as to form one or more irrigation holes 64, which are configured to allow irrigation fluid to flow out the insertion tube when irrigating the tissue of heart 26, for example during an ablation procedure.

Distal end assembly 40 further comprises a dome-cover 66, which is fabricated from a flexible PCB and configured to wrap around dome-support 68. In some embodiments, dome-cover 66 may be glued to dome-support 68. In alternative embodiments, cover 66 may be fabricated from a liquid crystal polymer (LCP) PCB, which may be formed (e.g., thermoformed) into a cup shape and bonded to sheet 60. The cup shape may be bonded to dome-support 68 and sheet 60 bonded to base 58 using any suitable bonding technique known in the art.

In some embodiments, sheet 60 and cover 66 are made from a single piece of contiguous PCB or any other suitable flexible substrate. In alternative embodiments, sheet 60 and cover 66 may be formed from separate pieces of material and coupled to one another using welding or any other suitable coupling technique.

Figure 3:
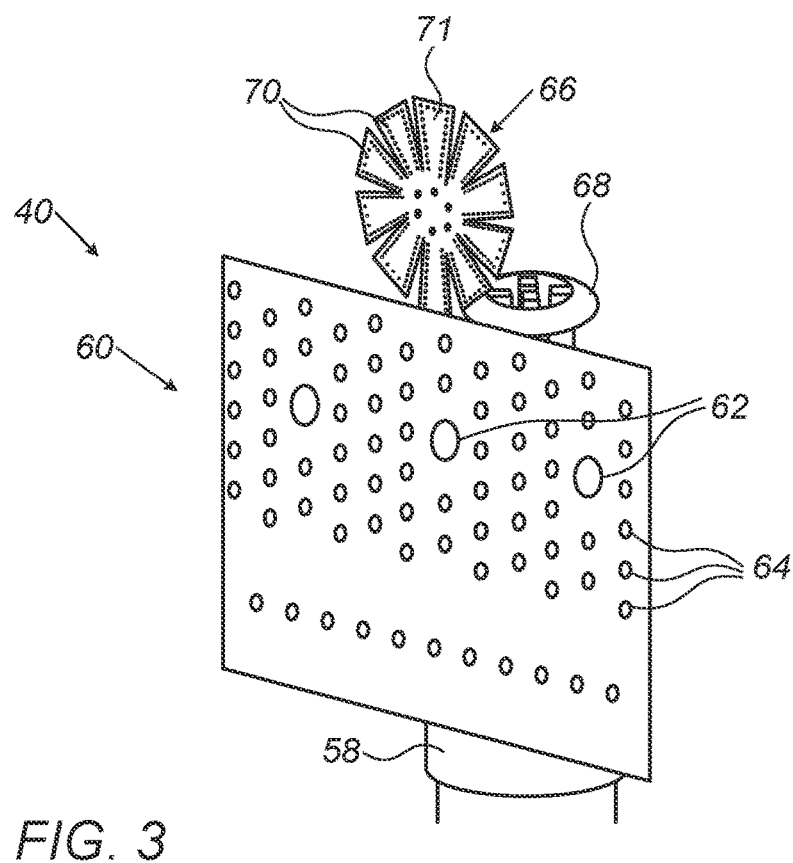

FIG. 3 is a schematic, exploded pictorial illustration of distal end assembly 40, in accordance with an embodiment of the present invention. FIG. 3 shows the opposite surfaces of sheet 60 and cover 66 from those shown in FIG. 2. In some embodiments, sheet 60 may comprise one or more micro-electrodes 62, which are configured to read signals and impedance. Cover 66 is intended to face internal tissue of heart 26 during the ablation procedure. In some embodiments, one or more thermocouples (not shown) may be embedded between the layers of PCB sheet 60. The thermocouples may be formed using PCB manufacturing techniques such as sputtering or be prepared in advance and embedded between the layers of sheet 60.

In an embodiment, cover 66 may comprise tip electrode 71, which is configured to ablate the internal tissue of heart 26. In some embodiments, cover 66 may comprise non-metallized plastic parts 70 formed on the PCB between sections of tip electrode 71. In an embodiment, parts 70 may be perforated so as to assist in bonding plastic parts 70 to the PCB.

Additionally or alternatively, distal end assembly 40 may comprise one or more position sensors that enable the magnetic position tracking system to measure and track its location in the body.

In the present context, tip electrode 71, micro-electrodes 62 and the thermocouples, thermistors and position sensors are regarded as examples of electrical devices coupled to the flexible substrate of the distal end assembly. In alternative embodiments, any other suitable types of electrical devices can be used, such as pressure sensors.

In some embodiments, micro-electrodes 62 and tip electrode 71 may be printed directly on PCB sheet 60 and on dome-cover 66, respectively. In alternative embodiments, at least some of the electrodes (e.g., micro-electrodes 62) may be mounted, for example, on sheet 60 on either the inside or the outside and bonded to the electrical interconnections. The electrical devices may be electrically connected to console 24 via the electrical interconnections comprised in sheet 60 and cover 66, and the wiring traversing catheter 22.

Figure 4:
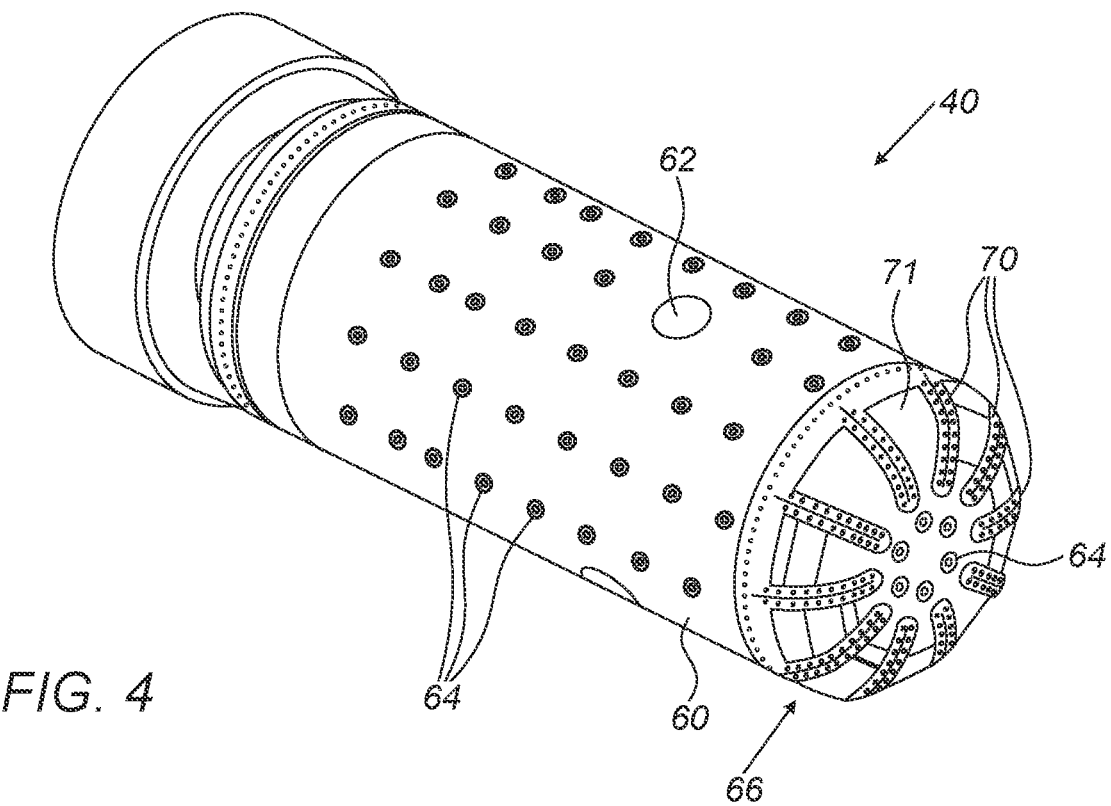
FIG. 4 is a schematic, pictorial illustration of a distal end assembly of a catheter, in accordance with an embodiment of the present invention.

FIG. 4 is a schematic, pictorial illustration of distal end assembly 40, in accordance with an embodiment of the present invention. PCB sheet 60 and dome-cover 66 are wrapped around member 69 so that irrigation holes 64 and the electrical devices, such as micro-electrodes 62 and tip electrode 71, are facing the internal tissue of heart 26.

The configuration of distal end device 40 shown in FIGS. 2-4 is an example configuration that is chosen purely for the sake of conceptual clarity. In alternative embodiments, any other suitable configuration can be used. For example, the flexible substrate used for implementing the distal end device may comprise any other suitable substrate, not necessarily a PCB.

In alternative embodiments, rather than having a skeleton shape, the distal end assembly comprises a contiguous hollow insertion tube made of plastic or any other suitable material, and having a cap at its distal tip. The insertion tube is configured to form an internal lumen for leading electrical wires and/or irrigation tubes via catheter 22. In this embodiment, at least some of the electrical interconnections and insulating films described above may be disposed as a flexible substrate directly onto the insertion tube, using plating or any other suitable disposing techniques.

At least one of the disposed films (e.g., the outermost film) may be biocompatible so as to allow direct physical contact between the distal end assembly and the heart tissue. Furthermore, the electrodes or other electrical devices may be directly plated on the insertion tube, or coupled to the tube after forming the electrical interconnections. In an embodiment, the insertion tube may be perforated so as to form the irrigation holes using very large scale integration (VLSI) processes known in the art, such as deposition (e.g., sputtering, physical vapor deposition (PVD) and plating), patterning (e.g., direct deposition on masks or photo-lithography and etching) and/or laser drilling for perforating the irrigation holes in the insertion tube.

Although the embodiments described herein mainly address ablation catheters, the methods and systems described herein can also be used in any other suitable medical probe, such as sinuplasty and neurosurgical procedures.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method for producing a catheter, comprising:
providing an internal member having a base connected to a ring-shaped dome support by multiple ribs that extend from the base, the ring-shaped dome support located at an apex of a distal end of the internal member;
wrapping a sheet of a first flexible substrate around the distal end of the internal member to form a tube that extends from the base of the internal member, wherein the first flexible substrate comprises one or more electrical interconnections and the first flexible substrate includes first and second edges;
coupling one or more electrical devices to the first flexible substrate;
forming a sheet of a second flexible substrate into a dome-cover to wrap around the ring-shaped dome support of the internal member and coupled to the tube formed by the first flexible substrate, the dome-cover comprises a tip electrode with non-metallized parts disposed between sections of the tip electrode; and perforating the non-metallized parts of the sheet of second flexible substrate so as to form irrigation holes.

2. The method according to claim 1, wherein the providing the internal member comprises providing a hollow internal member so as to form an internal lumen for leading one or more electrical wires to the distal end.

3. The method according to claim 1, wherein the providing the internal member comprises providing a hollow internal member so as to form an internal lumen for leading one or more irrigation tubes to the distal end.

4. The method according to claim 1, wherein wrapping the sheet of first flexible substrate comprises wrapping a flexible printed circuit board (PCB), and wherein the one or more electrical interconnections comprise conductive traces.

5. The method according to claim 1, wherein wrapping the sheet of first flexible substrate comprises directly plating the distal end with one or more films so as to form the one or more electrical interconnections and the one or more electrical devices.

6. The method according to claim 1, wherein coupling the one or more electrical devices comprises coupling one or more thermocouples.

7. The method according to claim 1, wherein coupling the one or more electrical devices comprises coupling one or more position sensors.

8. The method according to claim 1, wherein the sheet of the first flexible substrate and the sheet of second flexible substrate in the form of a dome-cover comprise a single contiguous section of flexible substrate.

9. The method according to claim 1, wherein wrapping the sheet of first flexible substrate comprises welding the first and second edges of the sheet of first flexible substrate to one another.

10. The method according to claim 1, wherein the forming comprises gluing the dome-cover to the apex of the distal end.

11. The method according to claim 1, wherein forming the dome-cover comprises thermoforming a liquid crystal polymer (LCP) PCB.

* * * * *